US007896821B1

(12) United States Patent
Magnin et al.

(10) Patent No.: US 7,896,821 B1
(45) Date of Patent: Mar. 1, 2011

(54) LOW INTENSITY DIRECTED ULTRASOUND (LODUS) MEDIATED BLOOD BRAIN BARRIER DISRUPTION

(75) Inventors: Paul A. Magnin, Andover, MA (US); Ulrich Herken, Medford, MA (US); Albert S. Kyle, Andover, MA (US)

(73) Assignee: Perfusion Technology, LLC, Lawrence, MA (US)

( * ) Notice: Subject to any disclaimer, the term of this patent is extended or adjusted under 35 U.S.C. 154(b) by 1381 days.

(21) Appl. No.: 10/987,398

(22) Filed: Nov. 12, 2004

Related U.S. Application Data

(60) Provisional application No. 60/559,943, filed on Apr. 6, 2004, provisional application No. 60/520,144, filed on Nov. 14, 2003.

(51) Int. Cl.
*A61H 1/00* (2006.01)
(52) U.S. Cl. .......................................... 601/2
(58) Field of Classification Search ................. 600/407, 600/437, 439; 604/22, 28, 511, 500, 501, 604/522, 518, 898; 601/2–4
See application file for complete search history.

(56) References Cited

U.S. PATENT DOCUMENTS 5,752,515 A * 5/1998 Jolesz et al. ................. 600/458
6,514,221 B2 * 2/2003 Hynynen et al. ................ 601/2
2003/0009153 A1 * 1/2003 Brisken et al. ........... 604/890.1

OTHER PUBLICATIONS

Akiyama et al., Abstract of "Low-frequency Ultrasound Penetrates the Cranium and Enhances Thrombolysis In Vitro," Neurosurgery 43:828-833 (1998).
Alexandrov, "High Rate of Recanalization and Dramatic Clinical Recovery During tPA infusion When Continuously Monitored With 2-MHz Transcranial Doppler Monitoring," Stroke 31:610-614 (1998).
Bao et al., "Transfection of a Reporter Plasmid Into Cultured Cells by Sonoporation," Ultrasound in Med. & Biol. 23:953-959 (1997).
Behrens et al., "Low-Frequency, Low-Intensity Ultrasound Accelerates Thrombolysis Through the Skull," Ultrasound in Med. & Biol. 25(2):269-273 (1999).
Black et al., "Modulation of Brain Tumor Capillaries for Enhanced Drug Delivery Selectively to Brain Tumor," Maxine Dunitz Neurosurgical Institute and Burns and Allen Research Institute, Cancer Control, 11(3):165-173 (2004).
Carstensen et al., "The Search for Cavitation In Vivo," Ultrasound in Med. & Biol. 26(9): 1377-1385 (2004).
Church C., "Spontaneous Homogenous Nucleation, Inertial Cavitation in vivo," Ultrasound in Med. & Biol. 28(10):1349-1364 (2002).

(Continued)

*Primary Examiner*—Tse Chen
*Assistant Examiner*—Elmer Chao
(74) *Attorney, Agent, or Firm*—Cesari and McKenna, LLP; Martin J. O'Donnell

(57) ABSTRACT

A method and device selectively and reversibly disrupts the blood-brain barrier (BBB) in a selected volume of the brain without the need for exogenous agents. The method and device employ low intensity directed ultrasound (LODUS) that is safe, reduces the danger of cavitation and thermal tissue damage, and is able to expose small or large regions of the brain to achieve a desired therapeutic or prophylactic effect.

4 Claims, 8 Drawing Sheets

OTHER PUBLICATIONS

Fellner et al., "Transport of paclitaxel (Taxol) across the blood-brain barrier in vitro and in vivo" J. Clin. Invest. 110(9):1309-18 (2002).
Francis et al., "Ultrasound accelerates transport of recombinant tissue plasminogen activator into clots," Ultrasound in Med. & Biol. 21(3): 419-24 (1995).
Goodman and Gilman, *The Pharmacological Basis of Therapeutics*, 7th Ed., Macmillan Publishing Co., New York, pp. 5-13 (1985).
Groothuis, "The blood-brain and blood-tumor barriers: A review of strategies for increasing drug delivery," Neuro-Oncology 2:45-59 (2000).
Guzman H.R., Abstract of "Ultrasound Mediated Disruption of Cell Membranes, Quantification of molecular uptake and cell viability," Acoustic Soc. Am. 2001 10(1) 588-596 (2001).
Hiesiger et al., Abstract of "Opening the Blood-Brain and Blood-Tumor Barriers in Experimental Rat Brain Tumors: The Effect and Intracarotid Hyperosmolar Mannitol on Capillary Permeability and Blood Flow," Annals of Neurology, 19:50-59 (1986).
Huber, Abstract of "Focused ultrasound (HIFU) induces localized enhancement of reporter gene expression in rabbit carotid artery," Gene Therapy, 10:1800-1807 (2003).
Huber et al., "Molecular physiology and Pathophysiology of tight junctions in the blood-brain barrier," Trends Neuroscience 24(12): 719-725 (2001).
Hynynen, "Trans-skull Ultrasound Therapy: The Feasibility of Using Image-Derived Skull Thickness Information to Correct the Phase Distortion," IEEE Transactions UFFC 46(3):752-755 (1999).
Hynynen et al., "MRI Guided Focal Blood Brain Barrier Opening Using focused Ultrasound" Ultrasonics Symposium p. 1417 (2000).
Hynynen et al.,"Noninvasive MR imaging-guided focal opening of the blood-brain barrier in rabbits" Radiology 220(3): 640-646 (2001).
Hynynen et al., "The Threshold for Brain Damage in Rabbits induced by Bursts of Ultrasound in the Presence of an Ultrasound Contrast Agent (Optison®)," Ultrasound in Med. & Biol. 29(3):473-481 (2003).
Hynynen et al., "Local and reversible blood-brain barrier disruption by noninvasive focused ultrasound at frequencies suitable for trans-skull sonications," NeuroImage 24:12-20 (2005).
Karshafian et al., "How do Ultrasound & Microbubbles Influence Drug Uptake?" U. Toronto, Conference Poster.
Kim et al., "Ultrasound-Mediated Transfection of Mammalian Cells," Human Gene Therapy 7: 1339-1346 (1996).
Kroll et al., Abstract of "Improving drug delivery to intracerebral tumor and surrounding brain in a rodent model: a comparison of osmotic versus bradykinin modification of the blood-brain and/or blood-tumor barriers," Neurosurgery 43(4):879-86 (1998).
Kudo S., "Thrombolysis with Ultrasound Effect," Tokyo Jikeikai Medical J. 104:1005-1012 (1989).
Li et al., "Gene Transfer with Echo-enhanced Contrast Agents," Radiology (2003).
Luo et al., "Transcutaneous ultrasound augments lysis of arterial thrombi in vivo" 94(4):775-778 (1996).
Maruvada et al., "Optical Monitoring of Ultrasound-Induced BioEffects in Glass Catfish," Ultrasound in Med. & Biol. 30(1): 67-74 (2004).
Mesiwala et al., "High-Intensity focused ultrasound selectively disrupts the blood-brain barrier in vivo," Ultrasound in Med. & Biol. 28(3): 389-400 (2002).
Miller et al., "Sonoporation of monolayer cells by diagnostic ultrasound activation of contrast-agent gas bodies," Ultrasound in Med. & Biol. 26: 661-667 (2000).
Molnar et al., Abstract of "The blood-brain barrier in primary CNS lymphomas: Ultrastructural evidence of endothelial cell death" Neuro-oncology 1(2):89-100 (1999).
Muldoon et al., "Comparison of intracerebral inoculation and osmotic blood-brain barrier disruption for delievery of adenovirus, herpesvirus, and iron oxide particles to normal rat brain," Am. J. Path. 147(6): 1840-1851 (1995).
Nag S., "Morphology and Molecular Properties of Cellular Components of Normal Cerebral Vessels," *The Blood-Brain Barrier: Biology and Research Protocols*, p. 3-36 (2003).
E.A. Neuwelt, Abstract of "Mechanisms of disease: the blood brain barrier," Neurosurgery 54(1):131-40 (2004).
Neuwelt et al., Abstract of "Cerebrovascular permeability and delivery of gentamicin to normal brain and experimental brain abscess in rats," Journal of Neurosurgery 61:430-439 (1984).
Neuwelt and Dahlborg, "Blood-Brain barrier disruption in the treatment of brain tumors: Clinical Implications," *Implications of the blood-brain barrier and its Manipulation*, p. 195-261 (1989).
W. M. Pardridge, Abstract of "Drug and Gene Targeting to the Brain with Molecular Trojan Horses," Nature Reviews Drug Discovery 1:131-139 (2002).
Patrick et al., Abstract of "Ultrasound and the Blood-Brain Barrier," Adv. Exp. Med. Biol. 267:369-381 (1990).
Prados et al., Abstract of "A randomized, double-blind, placebo-controlled, phase 2 study of RMP-7 in combination with carboplatin administered intravenously for the treatment of recurrent malignant glioma," Neuro-oncology 5(2): 96-103 (2003).
Poliachik et al., "Activation, Aggregation and Adhesion of Platelets Exposed to High-Intensity Focused Ultrasound," Ultrasound in Med. & Biol. 27(11):1567-1576 (2001).
Remsen et al., Abstract of "The Influence of anesthetic choice, PaCO2, and other factors on osmotic blood-brain barrier disruption in rats with brain tumor xenografts," Anesth. Analg. 88(3): 559-567 (1999).
Riggs et al., Abstract of "Ultrasound enhancement of rabbit femoral artery thrombolysis," Cardiovasc. Surg. 5(2):201-207 (1997).
Sheikov et al., "Cellular Mechanisms of the Blood-Brain Barrier Opening Induced by Ultrasound in Presence of Microbubbles," Ultrasound in Med. & Biol. 30(7):979-989 (2004).
Suchkova et al., "Effect of 40-kHz ultrasound on acute thrombotic ischemia in a rabbit femoral artery thrombosis model: enhancement of rabbit and improvement in capillary muscle perfusion," Circulation 101(19): 2296-2301 (2000).
Suchkova et al., "Ultrasound improves tissue perfusion in ischemic tissue through a nitric oxide dependent mechanism," Thromb. Haemost. 88(5): 865-870 (2002).
Tezel et al., Abstract of "Frequency Dependence of Sonophoresis," Pharmaceutical Research 18(12) :1694-1700 (2001).
Vykhodtseva et al., "Histologic Effects of High Intensity Pulsed Ultrasound Exposure With Subharmonic Emission in Rabbit Brain In Vivo," Ultrasound in Med. & Biol. 21(7):969-979 (1995).

* cited by examiner

LOW INTENSITY DIRECTED ULTRASOUND (LODUS) MEDIATED BLOOD BRAIN BARRIER DISRUPTION

CROSS-REFERENCE TO RELATED APPLICATIONS

The present application claims the benefit of U.S. Provisional Patent Application Ser. No. 60/520,144, entitled Perfusion Technology, which was filed on Nov. 14, 2003, by Albert Kyle and is hereby incorporated by reference as though fully set forth herein.

The present application also claims the benefit of U.S. Provisional Patent Application Ser. No. 60/559,943, entitled Ultrasound Therapy, which was filed on Apr. 6, 2004, by Albert Kyle and is hereby incorporated by reference as though fully set forth herein.

FIELD OF THE INVENTION

This invention generally relates to opening the blood-brain barrier to therapeutic agents that normally would not pass in therapeutic concentrations to tissue protected by the blood-brain barrier, and more specifically to an apparatus and method for applying low intensity directed ultrasound ("LODUS") for opening the blood-brain barrier.

BACKGROUND OF THE INVENTION

The blood brain barrier ("BBB") is formed by layers of cells lining the cerebral vasculature. As such, the BBB is able to maintain a stable environment in the brain by preventing the entrance of most substances such as toxins, drugs, viruses and bacteria from the blood stream into brain tissue. The blood brain barrier typically prevents trans-port of molecules larger than about 180 Daltons because of tight endothelial junctions (zonulae occludens), glial processes and basal lamina and the lack of fenestrations and transendothelial channels in the blood vessels' linings. It is also believed that permeability through the BBB may be further limited by the active transport of foreign substances out of the brain and into the lumen of the cerebral vasculature.

The BBB presents one of the largest obstacles to treating many brain diseases. Specifically, the BBB prevents many therapeutic agents, such as drugs and gene-therapy vectors, from accessing a patient's brain tissue. For example, infections of the central nervous system, neurodegenerative diseases, congenital enzyme defects and brain cancer are all affected by the ability of the BBB to block passage of, inter alia, antibiotics, anti-retroviral drugs, enzyme replacement therapy, gene preparations and anti-neoplastic drugs. As a result, diseased brain tissue often cannot receive the necessary amounts of therapeutic agents to properly heal. It is therefore generally desirable to temporarily "open" the BBB to permit therapeutic quantities of these agents to access the brain tissue in a safe, controlled and reversible manner, i.e., without damaging the brain tissue or its blood vessels and without permitting access permanently or for an extended period of time.

In brain tumors, the BBB inside the tumor (the "blood-tumor barrier," or "BTB") frequently exhibits a greater degree of permeability than the BBB located elsewhere in the brain. This is due to fenestrations in the tumor's endothelial cell layer and possibly also due to endothelial cell death in the tumor. Despite its relatively greater permeability, the BTB rarely permits sufficient amounts of therapeutic agents to be transported from the blood to the cancerous brain tissue. Like the BBB, the BTB also suffers the problem of inhibiting delivery of therapeutic agents. Thus, in discussing the delivery of therapeutic quantities of drugs for the treatment of brain cancer as set forth herein, the "BBB" will be broadly construed to include the blood-tumor barrier or "BTB."

Previous attempts have been made to penetrate the BBB with therapeutic agents. In particular, prior research indicates that BBB permeability may be increased by (i) infusing hyperosmolaric solutions, such as mannitol, in close proximity to the BBB; (ii) administering drugs, such as bradykinin, intra-venously or intra-arterially; or (iii) disrupting the BBB by delivering focused energy to it. Each of these prior techniques suffers various disadvantages that limit its practical application.

Mannitol

Osmotic substances, most notably mannitol, have been used for decades to increase BBB permeability for drugs like methotrexate, carboplatin, and others. A catheter is placed into the internal carotid artery of a patient on the side where BBB disruption is intended. Mannitol solution is then rapidly infused, frequently followed by an intra-arterial injection of a drug. This method has demonstrated that an unspecific disruption of the BBB can be used to deliver the drug to the brain. See Neuwelt et al, *Blood-Brain Barrier Disruption in the Treatment of Brain Tumors: Clinical Implications*, in *Implications of the Blood-Brain Barrier and Its Manipulation*, Neuwelt, Editor: p. 195-253 (1989).

Although a positive effect on BBB permeability has been shown by such treatments, use of osmotic substances has not been widely adopted. The necessity for placement of an intra-arterial catheter prior to each drug treatment is cumbersome. Further, the mannitol injection is often associated with seizures and sometimes hemorrhages. Moreover, the resultant BBB opening occurs in the whole hemisphere treated, and it is difficult to control how long the BBB opening will persist.

Bradykinin

Other attempts to open the BBB with bradykinin or analogous substances showed early promising results. See, for example, Kroll et al, *Improving drug delivery to intra-cerebral tumor and surrounding brain in a rodent model: a comparison of osmotic versus bradykinin modification of the blood-brain and/or blood-tumor barriers*, Neurosurgery 43(4): p. 879-86 (1998). In these studies, the effect of bradykinin appeared to be mostly limited to the BTB. Specifically, bradykinin drugs increased the permeability of the BTB, with the additional advantage of permitting therapeutic drugs to be administered relatively easily via intra-venous injection.

Despite its above-noted advantages, the use of bradykinin drugs has some significant drawbacks that renders it impractical for improving drug delivery through the BBB. For instance, the effect of bradykinin is not targeted to a specific region of the BBB and may inadvertently expose healthy brain tissue to potentially noxious substances. Specifically, bradykinin drugs may increase the permeability of a patient's entire BBB even though the therapeutic drug delivery is intended for only a specific region of the brain (e.g., a brain tumor). This overall increase in BBB permeability has the undesired effect of increased exposure of healthy brain tissue to various toxins circulating in the blood.

Blocking Transporter Proteins

If a therapeutic drug is a substrate of a specific ATP Binding Cassette ("ABC") transporter protein, inhibition of that transporter often enables the drug to move more easily across the BBB. Thus, transporter inhibition can be used to selectively increase the permeability of the BBB for the therapeutic drug. P-glycoprotein ("PGP"), for example, has a large number of known substrates, such as all glucocorticoids, doxorubicin, HIV protease inhibitors, phenytoin, taxol, and many others. It is apparent that treatment of a wide range of diseases is affected by just this one transporter protein. In fact, recent studies indicate that a substance blocking PGP could be used to enhance delivery of the drug paclitaxel across the BBB. See Fellner et al, *Transport of paclitaxel (Taxol) across the blood-brain barrier in vitro and in vivo*, J. Clin. Invest. 110(9): p. 1309-18 (2002).

Although blocking certain ABC transporter proteins, such as PGP, can reduce the vulnerability of the brain caused by a generalized increase of BBB permeability, this method is currently limited in its clinical application. For instance, because all substances that are substrates of the blocked transporter are permitted to pass through the BBB, some potentially dangerous substrates inadvertently may be able to penetrate the BBB. Further, ABC transporters may be expressed in other tissues besides the BBB. For example, PGP can also be found in the intestine, kidneys, gonads, placenta, hepatocytes, leucocytes and adrenal glands. Blocking PGP will therefore have a systemic effect and may, among other side-effects, cause an increased toxicity of its substrates. Another limitation of this approach is that drugs that are not a transporter substrate could not be delivered using this method. In summary, the PGP blocking method is limited because of its inability to deliver a wide variety of drugs to specific regions of the brain.

High Intensity Focused Ultrasound

Researchers have investigated the use of high intensity focused ultrasound ("HIFU") to selectively disrupt the BBB for the purpose of transporting therapeutic agents to the brain. Ultrasound having a frequency equal to or greater than 1 Megahertz (MHz) can be precisely focused to a volume as small as one cubic millimeter. By concentrating the high-intensity ultrasonic energy on a relatively small region of the BBB, it is believed that the permeability of the exposed region is improved as a result of inertial cavitation and heating effects in the cerebral vasculature, i.e., the focused ultrasound beam may nucleate or otherwise enhance microbubble development along the luminal membrane of the blood vessels' lining. The applied HIFU energy causes these microbubbles to oscillate violently until they collapse (i.e., cavitate), thereby opening the BBB.

The region of the BBB affected by the HIFU insonation will typically exhibit increased permeability for extended periods of time; indeed, periods of increased permeability of 6 hours and, in some cases, up to 72 hours have been reported. See, for example, Hynynen et al., *Noninvasive MR imaging-guided focal opening of the blood-brain barrier in rabbits*, Radiology 220(3): p. 640-6 (2001), and Mesiwala et al., *High-Intensity Focused Ultrasound Selectively Disrupts the Blood-Brain Barrier In Vivo*, Ultrasound in Med. & Biol. 28(3): p. 389-400 (2002). This relatively long duration for which the affected region of the BBB remains permeable leaves the brain vulnerable to toxins from the blood and also increases the risk of brain edema.

Further, the application of high-intensity focused acoustic energy can also cause permanent biological damage in and around the BBB. For instance, the process of ablating portions of the BBB may cause, e.g., cell death or cell necrosis. HIFU also may be destructive to osseous tissue (bone) surrounding the insonicated region of the BBB. Specifically, the bone absorbs the ultrasound energy which, in turn, creates localized heating in the bone. In general, the higher the ultrasound frequency, the more pronounced is the energy absorption and the resulting temperature increase in the bone. To prevent heating of the bone during a HIFU procedure, a craniotomy may have to be conducted and part of the skull removed to safely apply the HIFU energy directly to the brain.

In addition to the above-noted biological dangers associated with HIFU, implementation of HIFU is impractical for several additional reasons. HIFU is applied to a relatively small volume (~1 mm$^3$) and is not well suited for treatment of larger volumes, e.g., as required in tumor therapy. Accordingly, to create sufficient disruption of the BBB in and around a tumor, a multitude of HIFU exposures typically must be applied to a series of adjacent, non-overlapping target volumes. This tends to be a very difficult and time-consuming process. To facilitate the process, HIFU is often coupled with image guidance systems, such as magnetic resonance imaging guidance, to ensure that the focused ultrasound energy is precisely targeted in the desired BBB regions. The necessity for image-guidance places yet a further constraint on the practical application of HIFU. For instance, HIFU may not be able to effectively treat a patient when the spread of diseased tissue cannot be fully visualized using current imaging technology.

Practical implementation of HIFU treatment is also limited by the instrumentation needed to apply HIFU. HIFU systems usually employ a complex phased array of ultrasound transducers, powered and controlled by a computer controller. The phased array applies focused ultrasound to those locations in the BBB targeted for treatment. These focused locations can be adjusted electronically using different relative phase excitations of the array elements. Alternatively, a concave surface transducer may be used to focus the ultrasound beam. In either case, the HIFU system typically comprises complex electronics which require sophisticated configuration and maintenance. As such, the HIFU system may require operators to consume substantial amounts of time and resources to maintain proper operation of the system.

Some researchers have experimented with exogenous agents, such as microbubble agents, in an attempt to improve the effectiveness of HIFU for opening the BBB. However, Karshafian et al. at the University of Toronto showed that the presence of an exogenous microbubble agent not only enhances the BBB permeability but also increases the amount of cell death resulting from the HIFU exposure, especially at lower ultrasonic frequencies. Thus, introduction of the microbubble agent does not appear to remedy the deficiencies of HIFU, and in some cases may even render application of HIFU more dangerous. Also, the combination of three parameters—agent, drug and ultrasound energy—will require extensive validation of the combinations of doses of agent, drug and energy in order to ensure safety and effectiveness. This may represent a prohibitively costly barrier to prove feasibility of the method.

A new method to reversibly increase the permeability of the BBB is needed. Unlike current approaches, this method should be non-invasive to allow its wide-spread use. Regional selectivity with regard to where BBB disruption will occur is desirable. Further, the method should affect a volume of brain tissue large enough to include a complete tumor as well as its surrounding tissue.

SUMMARY OF THE INVENTION

The present invention overcomes the disadvantages of the prior art by increasing the permeability of the blood-brain barrier ("BBB") using low intensity directed ultrasound ("LODUS"). Unlike previous BBB disruption techniques, LODUS increases the BBB permeability in a controlled and reversible manner. Operationally, one or more unfocused ultrasound beams are generally directed to a region of the brain requiring therapy. These directed beams emit ultrasound using lower intensities and frequencies than those used in conventional high-intensity focused ultrasound ("HIFU") applications. The relatively long-wavelength LODUS beams may be used to affect a larger region of the brain, e.g., they will not only affect cancerous tissue in a tumor, but also its penumbra, which also may contain malignant tissue. The intensity and frequency of the LODUS beams are selected so that enough energy is transmitted to grow and oscillate microbubbles at the targeted location in the direct vicinity of the BBB, although not enough energy is applied to cause the traditional inertial cavitation and heating effects associated with HIFU. As a result, the oscillating microbubbles are able to transiently disrupt the BBB through mechanical interaction with the endothelial cells, without causing permanent damage to the BBB or its surrounding tissue. The LODUS method can avoid the introduction of exogenous microbubbles by using endogenous bubbles already present in the blood of the patient. By careful selection of various LODUS parameters, endogenous bubbles can grow and maintain stable oscillations at the targeted region. These oscillating endogenous microbubbles are able to transiently disrupt the targeted BBB through mechanical action, thereby avoiding the introduction of exogenous agents. Because LODUS is reversible and employs relatively low intensity levels, LODUS provides a safe, effective approach for enhancing drug delivery across the BBB.

In accordance with the illustrative embodiments, LODUS insonation is provided by means of a headpiece which is snugly fitted on a patient's head. The headpiece contains one or more ultrasound transducers that are strategically mounted on the headpiece to supply low intensity directed ultrasound to a desired region of the patient's BBB. The transducer or transducers may be directly integrated into the headpiece, or alternatively may be integral units attached to the headpiece. Each transducer is preferably adapted to apply a substantially uniform pressure against the head of the patient, thereby reducing energy loss and possible heating effects between the transducer and the patient's skin.

Those skilled in the art will appreciate that many different configurations of LODUS transducers are possible on the headpiece. For instance, in a first illustrative embodiment, a single LODUS transducer may be positioned to provide a regional therapeutic effect. In a second illustrative embodiment, a plurality of transducers may be positioned to provide an additive effect at a specific region located at the intersection of the transducers' emitted LODUS beams. Because of the relatively large wavelength of the intersecting LODUS beams, the affected BBB region may occupy a relatively large volume, e.g., on the order of thousands of cubic millimeters or more. In yet another embodiment, a set of transducers may be positioned along the headpiece, and the transducers may be coordinated to apply a uniform acoustic pressure throughout a substantial portion of the patient's brain.

To effectuate LODUS ultrasound delivery through the skull, an operating frequency is selected between approximately 200 kilohertz (kHz) and 2 MHz. This frequency range is sufficiently high that it is not "heard" by the patient, e.g., via ultrasonic bone conduction which may be interpreted by the cochlea as an audible sound. Yet, this frequency range is still within a range that allows sufficient energy to pass through the skull and into the treatment region to provide meaningful therapeutic (or prophylactic) effect. In a preferred embodiment, the ultrasound transducer is driven at a frequency of approximately 300 kHz. The intensities of the LODUS ultrasonic beams are characterized by mechanical index values that are less than one and preferably in the range of 0.1 to 0.6.

Each LODUS transducer is configured to emit a relatively long train of ultrasound pulses, e.g., comprising several hundred pulses, at the selected ultrasound frequency. The transducers are driven to repeat their respective pulse trains, preferably at a pulse repetition frequency in the range from about 10 Hertz (Hz) to 10 kHz. The duration of the pulse trains is preferably between 10 microseconds (µs) and 10 milliseconds (ms).

The LODUS approach described herein exhibits significant advantages over prior techniques for disrupting the BBB to facilitate therapeutic drug delivery. For example, LODUS exposes a larger volume of the BBB as compared with focused ultrasound techniques, such as HIFU. The larger region of exposure can be a benefit in treating certain neurological conditions (e.g., stroke, cancer, epilepsy and others) where the precise site of therapy is not well defined. A highly focused approach is more likely to "miss" or only partially cover the targeted region. Moreover, because LODUS utilizes lower intensities and frequencies than conventional focused ultrasound techniques, LODUS enables therapy to be applied for longer periods of time without inflicting harm to the patient. LODUS permits slower drug administration than short-acting BBB opening methods like, e.g., mannitol infusion, thereby providing better control over the rate and amount of drugs administered. For instance, certain drugs cause pain and trauma when given rapidly and thus slower administration can reduce these negative side effects. Slow intra-venous administration of a drug also permits termination of the infusion in the event of patient sensitivity. Because of the controlled and reversible nature of BBB disruption caused by LODUS, optimal drug concentration and increased BBB permeability can be timed to coincide.

Further, because LODUS employs lower frequencies than focused ultrasound techniques, there is less attenuation of energy at the skull bone and thus less heat generated at the patient's skin. To ensure that adequate therapeutic energy is delivered in situ, LODUS may be configured so that multiple transducers are positioned around the skull. This permits the multiple intersecting ultrasound beams to reinforce each other, while avoiding heating of a single high-intensity transducer site on the patient's skin. Since LODUS reduces heating of the skull bone, the LODUS procedure can be performed without the need of a craniotomy, as is currently required in many HIFU applications.

Another advantage of LODUS is that it is easier to deploy than conventional BBB disruption techniques. For instance, LODUS ultrasound is directed by simple aiming techniques, such as physically orienting one or more transducers on a headpiece. Thus, LODUS eliminates the complexities of electronic focusing and reduces the need for image guidance. Furthermore, LODUS does not require application of any exogenous agents, such as microbubble agents. LODUS's ease of use is vital for certain therapies, including stroke and traumatic brain injury, in which the therapy must be administered quickly. This is also important when treatment is given by staff that has less experience and skill in targeted treatment (e.g. in an emergency room), compared with more specialized staff (e.g. interventional radiology labs).

The LODUS technique may be adapted for delivery of both therapeutic and prophylactic agents that have been introduced into the blood stream. Such agents may include, inter alia, chemotherapeutic agents, anti-inflammatory agents, hormones, ion channel modifiers, and neuroactive agents. LODUS also may be used to increase trans-port of various genetic materials across the BBB. Such genetic materials may include nucleic acids that can correct genetic deficiencies, accomplish genetic immunization or provide genetic alteration, among other capabilities. In general, the therapeutic agents may be administered using various means. For instance, they may be administered intra-venously, intra-arterially, orally, sub-cutaneously, intra-muscularly, sub-lingually or by suppositories, inhalation or any other delivery technique known in the art.

BRIEF DESCRIPTION OF THE DRAWINGS

The above and further advantages of the invention may be better understood by referring to the following description in conjunction with the accompanying drawings in which like reference numerals indicate identically or functionally similar elements, of which.

DETAILED DESCRIPTION OF ILLUSTRATIVE EMBODIMENTS

Figure 1:
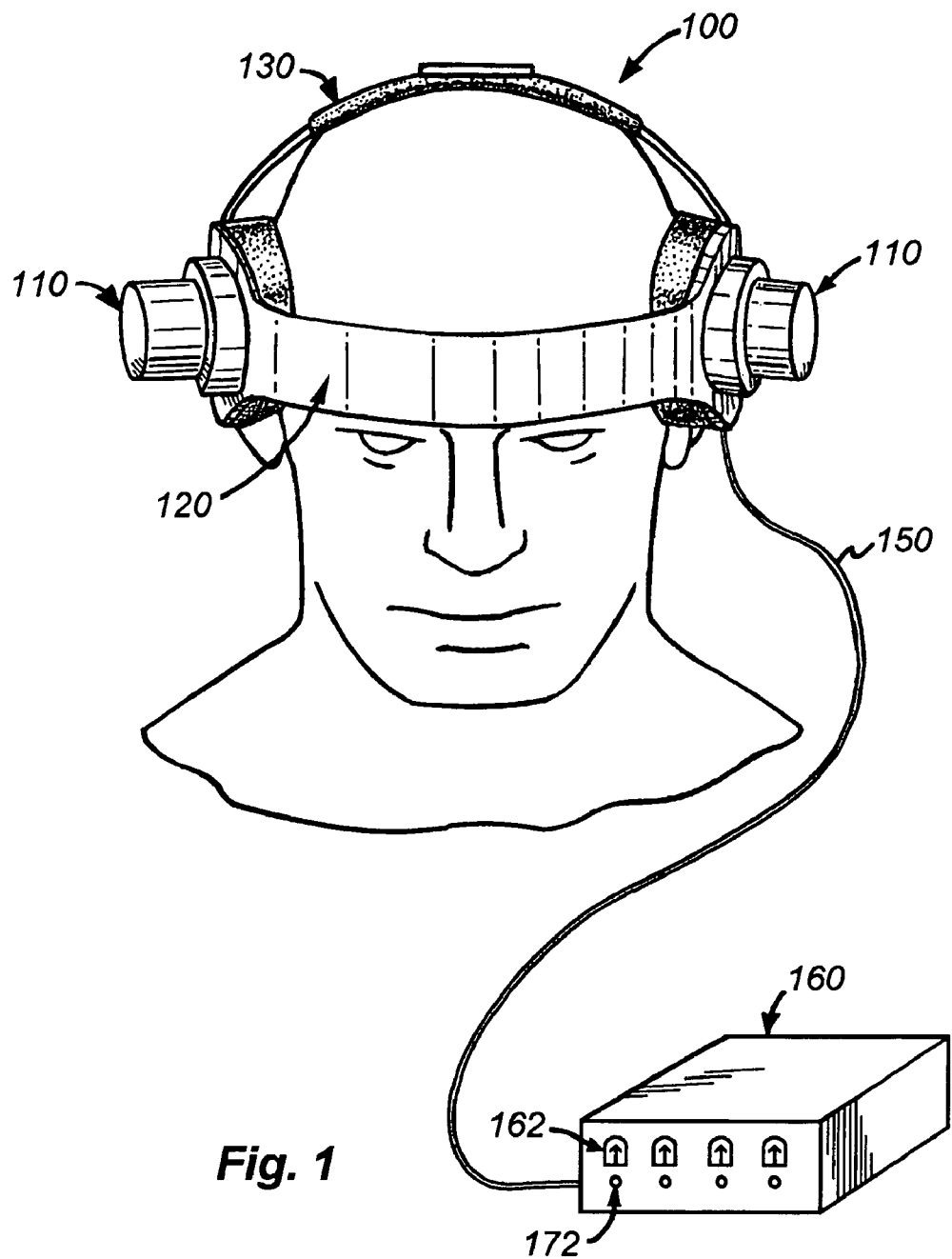
FIG. 1 is a front view of a headpiece structured to precisely mount and activate one or more low intensity directed ultrasound (LODUS) transducers in accordance with the illustrative embodiments.

FIG. 1 illustrates a headpiece 100 which may be used to apply low intensity directed ultrasound ("LODUS") for disrupting the blood-brain barrier ("BBB") in a controlled and reversible manner. The headpiece includes one or more LODUS transducers 110 which are strategically positioned along a circumferential band 120 adapted to fit securely around a patient's head, preferably encircling the head approximately at the level of the patient's temples. A top band 130 may be attached to the circumferential band 120 so as to span the diameter of the circumferential band. In this configuration, the top band 130 is seated atop of the patient's skull while the headpiece is worn, thereby preventing the headpiece from sliding vertically. It is expressly contemplated that the lengths of the bands 120 and 130 may be adjustable to accommodate heads of various shapes and sizes. Further, the bands may be constructed from various materials known in the art without limitation.

The LODUS transducers 110 are generally positioned to direct one or more beams of low-intensity ultrasound to a desired region of the patient's brain. Although the illustrative transducers shown are mounted on the circumferential band 120, it is also contemplated that one or more LODUS transducers may be positioned along the top band 130, or may be strategically positioned on the patient's head by other mounting means (not shown). The transducers may be mounted in fixed and/or adjustable orientations, i.e., capable of being repositioned in situ. Further, each transducer 110 may be directly integrated into the headpiece 100, or alternatively may be a self-contained element separately mounted to the headpiece. In operation, each LODUS transducer is firmly secured against the patient's skin to apply a uniform pressure against the head of the patient. As such, energy loss and heating effects between the transducer and the patient's skin are minimized.

A cooling system (not shown) may be employed to further minimize heating around the patient's skull. For example, a coolant, such as water, may be circulated around the transducers or disposed between the transducer and the patient's skin, e.g., by a coupling pad containing the coolant. Alternatively, the patient's head may be at least partially immersed in a water bath where the LODUS transducer or transducers is integrated into the water bath's enclosure. For example, the patient may be reclined backward until the patient's skull is submerged in the water bath, yet the patient's mouth and nose remain above the water line. The water bath not only provides coolant to dissipate heat at the interface of the transducers and the patient's skin, but also may provide better acoustic coupling for transmitting the LODUS waves to the targeted region of the patient's brain.

Figure 2:
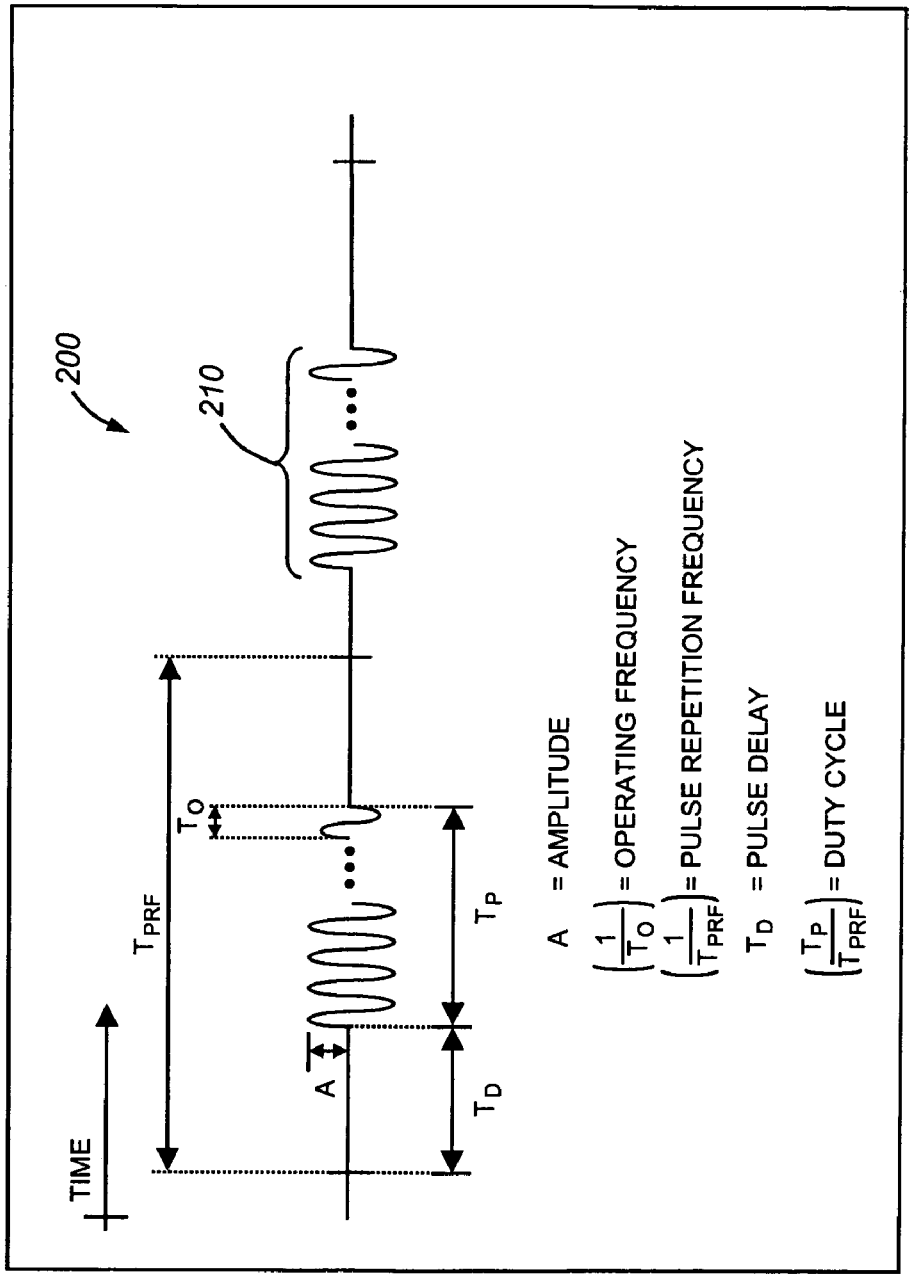
FIG. 2 is a partial time trace of an exemplary "drive" signal that may be used to activate a LODUS transducer in accordance with the illustrative embodiments.

The LODUS transducers 110 are driven by control electronics which may be integrated into the transducers or alternatively may reside in an external control module 160 coupled to the transducers by electrical leads 150. The control electronics generate electrical signals which activate ("drive") the transducers 110. FIG. 2 illustrates an exemplary electrical signal 200 that may be used to drive a LODUS transducer 110. The signal includes a pulse train 210 containing one or more time-varying pulses, each pulse having an amplitude A and a period $T_o$. Accordingly, the operating frequency of the signal 200 is defined as $(1/T_o)$. The pulse train is repeated after a predetermined time interval $T_{prf}$. Thus, the "pulse repetition frequency" of the drive signal 200 is defined as $(1/T_{prf})$. The pulse train 210 may be delayed within the predetermined time interval $T_{prf}$ by a time delay $T_d$. The number of pulses in the pulse train, or the "pulse length," defines the time duration $T_p$ of the pulse train. The duty cycle of the signal 200 is then defined as the ratio of $(T_p/T_{prf})$.

Returning again to FIG. 1, control electronics in the external control module 160 preferably generate separate signals 200 for activating each of the LODUS transducers 110. However, in some embodiments, the same drive signal may be input to more than one of the transducers. The control module 160 includes various indicators 162 and adjustable controls 172, such as knobs, that permit an operator to individually adjust selected LODUS parameters, such as operating frequency, amplitude, duty cycle, pulse rate frequency, pulse delay and so forth. In other words, each adjustment control 172 may select the value of a LODUS parameter whose value is displayed by a corresponding indicator 162, such as a conventional display gauge.

For example, each LODUS transducer 110 is preferably configured to emit a relatively long train of ultrasound pulses, e.g., comprising several hundred pulses, at the selected ultrasound frequency. Thus, the module 160 may include an adjustment control 172 for selecting the pulse repetition frequency $(1/T_{prf})$ of these pulse trains. Preferably, the selected pulse repetition frequency is within the range of about 10 Hertz (Hz) to 10 kHz. Another adjustment control may be used to select the duration $T_p$ of the pulse trains, e.g., preferably between 10 microseconds (μs) and 10 milliseconds (ms). Yet other adjustment controls 172 may select the time delays $T_d$ and amplitudes A of the pulse trains. Notably, each adjustment control on the control module 160 may be configured to adjust the value of a LODUS parameter for one or more of the transducers 110. Accordingly, a single set of controls 172 may be used to control the output of multiple LODUS transducers.

The LODUS transducers 110 are configured to deliver low-frequency ultrasound at relatively low intensity levels. Specifically, the intensity and frequency of the emitted ultrasound beams are selected so that enough energy can be transmitted through the patient's skull to grow microbubbles and maintain stable oscillations of those microbubbles at the targeted region of the patient's BBB. In this way, the oscillating microbubbles are able to transiently disrupt the targeted BBB through mechanical action at the endothelial cells, without causing potentially dangerous cavitation and heating effects conventionally associated with focused ultrasound treatments. Then, therapeutic or prophylactic agents present in the blood stream can penetrate the "opened" BBB region and effectively deliver therapy to the targeted brain cells.

To this end, the LODUS transducers 110 are configured to emit ultrasound having an operating frequency between approximately 200 kilohertz (kHz) and 2 MHz. This frequency range is sufficiently high that it is not "heard" by the patient, yet it provides a low enough frequency range to allow sufficient energy to pass through the skull for administering LODUS therapy. In a preferred embodiment, the LODUS transducers are driven at a frequency of approximately 300 kHz. The transducer's emitted ultrasound frequencies may be intentionally varied, e.g., by ±30 kHz or less, around their nominal 300 kHz center frequencies. By varying the driving frequencies input to a transducer, a more uniform time-averaged acoustic field can be applied to the targeted BBB region. That is, on average, the spatial peaks and nulls resulting from standing waves caused by reflections of the ultrasound beam inside a patient's skull may be reduced by introducing these frequency variations, and thus a "smoother" and more uniform LODUS field may be applied to the targeted region.

The intensities of LODUS ultrasonic beams are characterized by mechanical index (MI) values that are less than 1.0 and preferably in the range of 0.1 to 0.6. As conventionally understood, the mechanical index is a measure of ultrasound intensity and is defined as the peak rarefactional pressure of a propagating ultrasound wave expressed in Megapascals (MPa) divided by the square root of the wave's center frequency expressed in Megahertz (MHz). In the context of BBB disruption, ultrasound waves having larger MI values are more likely to cause inertial cavitation, and thus are more likely to damage blood vessels in the targeted BBB region. Furthermore, ultrasound waves having larger MI values are also more likely to cause heating of bone and tissue, potentially causing even more damage in those structures. Advantageously, the LODUS transducers 110 emit directed ultrasound waves whose MI values are sufficiently low to avoid permanent damage to the patient's BBB, yet provide sufficient energy delivery to open the BBB to therapeutic and/or prophylactic agents.

Various LODUS parameters may be selected to establish the desired MI value for a transducer 110. For instance, the control module 160 may comprise an adjustment control 172 that adjusts the amplitude of the transducer's emitted ultrasound wave. In an alternative embodiment, the control module may have an adjustment 172 that permits an operator to select the average power of the emitted ultrasound wave, such that the control electronics adjust at least one of the amplitude, duty cycle, or pulse repetition frequency of the signal 200 to achieve the desired output power level. In yet other embodiments, the module 160 may permit an operator to directly choose a desired MI value, then the control electronics automatically perform the necessary amplitude or power adjustments to output LODUS ultrasound beams at the desired MI value.

The control electronics in the module 160 are preferably configured to coordinate drive signals for a plurality of LODUS transducers. For instance, the relative time delays $T_d$ of the transducers' pulse trains may be adjusted so that the transducers' pulse trains arrive substantially simultaneously at a targeted BBB region. Alternatively, the relative timing of the transducers' pulse trains may be selected so as to provide a substantially continuous source of ultrasound energy to the targeted region. The amplitudes of the transducers' pulse trains may be adjusted to modulate the amount of energy delivered to the targeted region. Further, the control electronics may be configured to vary the operating frequency input to a plurality of LODUS transducers, e.g., to reduce the impact of standing waves in the brain cavity. Furthermore, the relative phase between the transducers' signals may be varied to reduce the impact of a plurality of standing waves overlapping each other.

The LODUS parameters characterizing the drive signal for a given transducer 110 may be manually selected by a system operator or may be automatically selected by the control electronics in the module 160. In the latter case, the control electronics may, for example, automatically adjust the relative phase or operational frequencies of the drive signals input to multiple LODUS transducers 110. In an illustrative embodiment, the relative phase of the drive signals input to a pair of transducers is modulated between in-phase (zero degree phase shift) and out-of-phase (180 degree phase shift) after every predetermined time interval $T_{prf}$. Alternatively, the relative phase shifts of the transducers' drive signals may be automatically adjusted to shift, e.g., 90 degrees, after every repeated interval $T_{prf}$. Further, the control electronics also may automatically select different operational frequencies input to the transducers. More generally, it is expressly contemplated that the control electronics may automatically control a desired combination of LODUS parameters based on any selected control or feedback algorithm.

In practice, a patient may receive a therapeutic agent prior to the LODUS insonation. For instance, the agent may be administered intra-venously, intra-arterially, orally, sub-cutaneously, intra-muscularly, sub-lingually or by suppositories, inhalation or any other delivery technique known in the art, such that the agent travels to the brain vasculature. The particular agent chosen is based on the particular problem being treated, such as neurodegenerative disease, brain cancer, genetic deficiencies, etc. Accordingly, the application of LODUS insonation opens the targeted BBB region and facilitates passage of the infused agent to the affected brain tissue. Typically, the targeted BBB region may be identified, e.g., based on previously-acquired images of the patient's brain. In other cases, the LODUS transducer 110 may be oriented to target a particular BBB region associated with the brain disease or disorder for which therapy is being applied.

Figure 3:
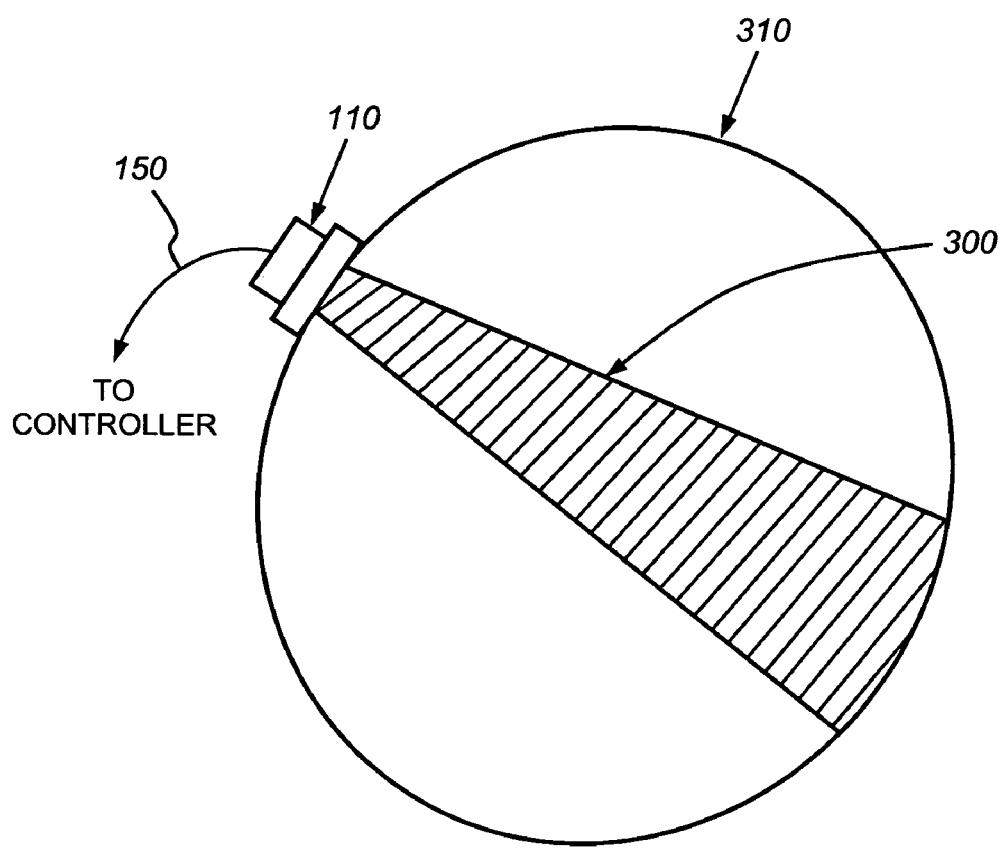
FIG. 3 is a side cross-sectional view of a LODUS transducer and a region of the brain affected by the transducer's emitted ultrasonic beam.

FIG. 3 illustrates a targeted region 300 of a patient's brain 310 which is exposed to a LODUS transducer's emitted ultrasonic beam. In accordance with the illustrative embodiments, the emitted LODUS beam is a repeated sequence of pulse trains, e.g., characterized by the various LODUS parameters selected in the control module 160. The transducer 110 may be mounted on the circumferential band 120 or along the top band 130 of the headpiece 100. The transducer is physically positioned to direct a low-intensity, low-frequency ultrasound beam to a desired region of the patient's BBB. As such, neither the patient nor the medical care provider has to manipulate sophisticated aiming instrumentation or complex image-guidance systems during the LODUS procedure, as required in conventional focused ultrasound techniques. The LODUS beam exposes a relatively large BBB region 300, e.g., on the order of thousands of cubic millimeters or more. Therapeutic or prophylactic agents present in the patient's blood stream can penetrate the targeted BBB region until the LODUS beam is removed and the affected region of the BBB reverts back to its original state.

Figure 4:
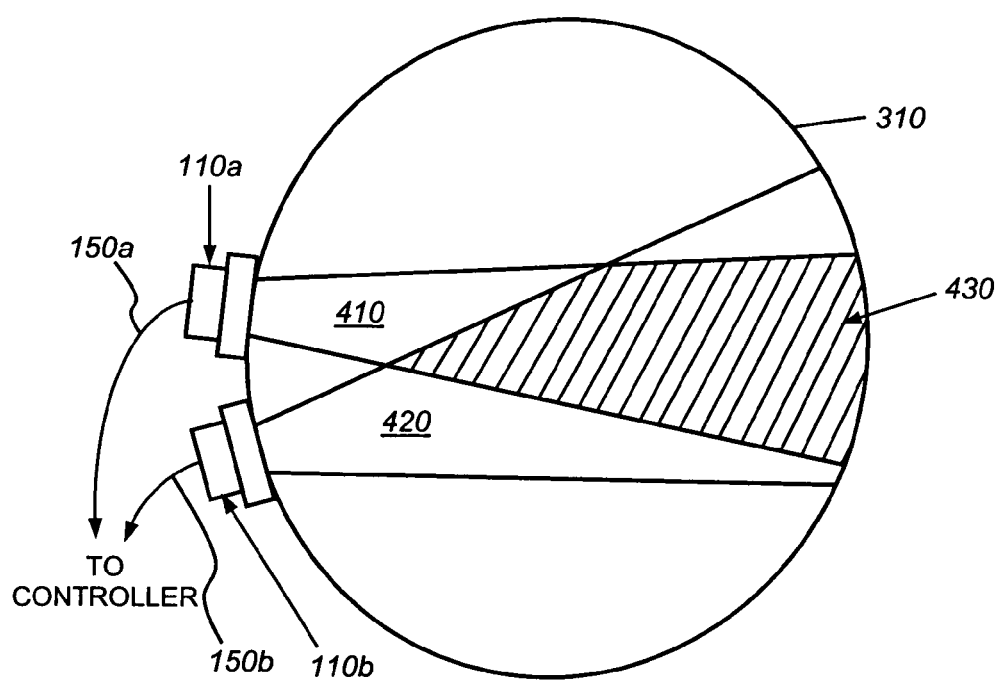
FIG. 4 is a side cross-sectional view of a pair of LODUS transducers mounted on the same side of a patient's brain and a region of the brain affected by the transducers' emitted ultrasonic beams.

FIG. 4 illustrates an exemplary LODUS treatment using first and second transducers 110a and 110b positioned in close proximity to one another. The first and second transducers may be individually positioned on the headpiece 100. Alternatively, they both may be situated within a closely-packed array of transducers mounted on the headpiece. The transducers are respectively coupled to the control module 160 by electronic leads 150a and 150b. Preferably, the control module outputs separate drive signals 200 for each of the transducers 110a and 110b. The first transducer 110a emits a LODUS ultrasound beam 410 covering a first region of the patient's brain 310. Similarly, the second LODUS transducer 110b emits a second ultrasound beam 420 that overlaps at least a portion of the first beam 410. The first and second beams intersect at a targeted BBB region 430. Preferably, the relative phase of the signal of the two transducers is varied from time to time to reduce the effects of nodes and anti-nodes that form in the target region 430 as a result of the interfering ultrasound beams. In this way, a more uniform LODUS field can be applied to the BBB in the target region.

Figure 5:
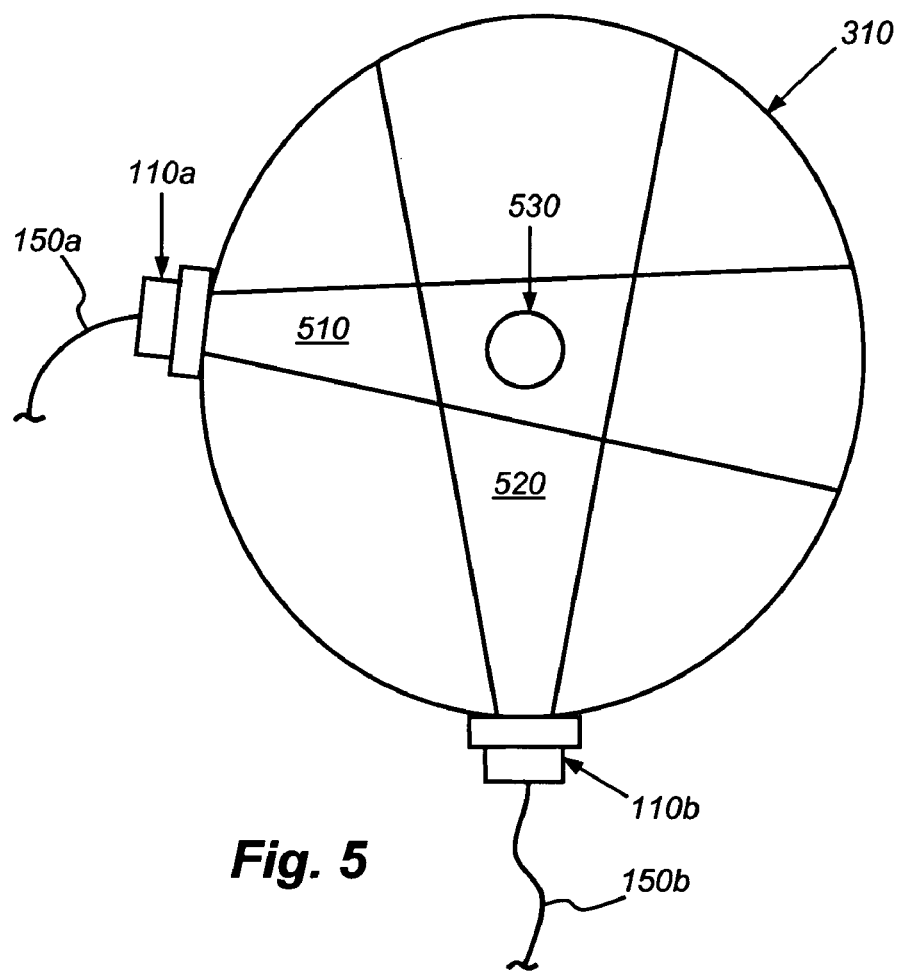
FIG. 5 is a top cross-sectional view of a pair of LODUS transducers strategically positioned around a patient's skull so the transducers' emitted beams expose a region known to include a brain tumor.

FIG. 5 illustrates an exemplary LODUS configuration for treating a brain tumor. First and second LODUS transducers 110a and 110b are strategically oriented on the patient's head so that their directed ultrasound beams, respectively labeled 510 and 520, intersect at the location of the brain tumor 530. The additive effect of the LODUS beams 510 and 520 increases the permeability of the BBB at the brain tumor (i.e., the brain-tumor barrier) without significantly affecting BBB permeability throughout the rest of the patient's brain 310. Unlike prior ultrasound techniques for treating brain tumors, LODUS benefits from utilizing low-frequency ultrasound that is not highly focused on the brain tumor. Specifically, the intersecting LODUS beams affect not only the cancerous tissue in the tumor, but also the surrounding penumbra which also may contain malignant tissue. Therefore, this LODUS configuration can affect cancerous cells in the tumor's penumbra that previously were outside the focal area, e.g., using HIFU insonation.

Illustratively, each of the LODUS beams 510 and 520 contains a sequence of pulse trains having a predetermined pulse repetition frequency, operating frequency, duty cycle, amplitude, etc., as determined by the control module 160. The pulse trains may be coordinated so they arrive at the brain tumor 530 at approximately the same time. In this case, the control electronics in the module 160 may modulate the frequency of the beams 510 and 520, e.g., after every emitted pulse train, to ensure that stationary nodes and anti-nodes do not persist in the targeted tumor region. Alternatively, the control electronics may time-multiplex the beams 510 and 520 so their respective pulse trains apply a substantially continuous stream of low-frequency, low-intensity ultrasound to the brain tumor 530. In either case, the control electronics may be configured to automatically sequence the pulse trains emitted from the first and second transducers 110, both spatially and temporally.

Figure 6:
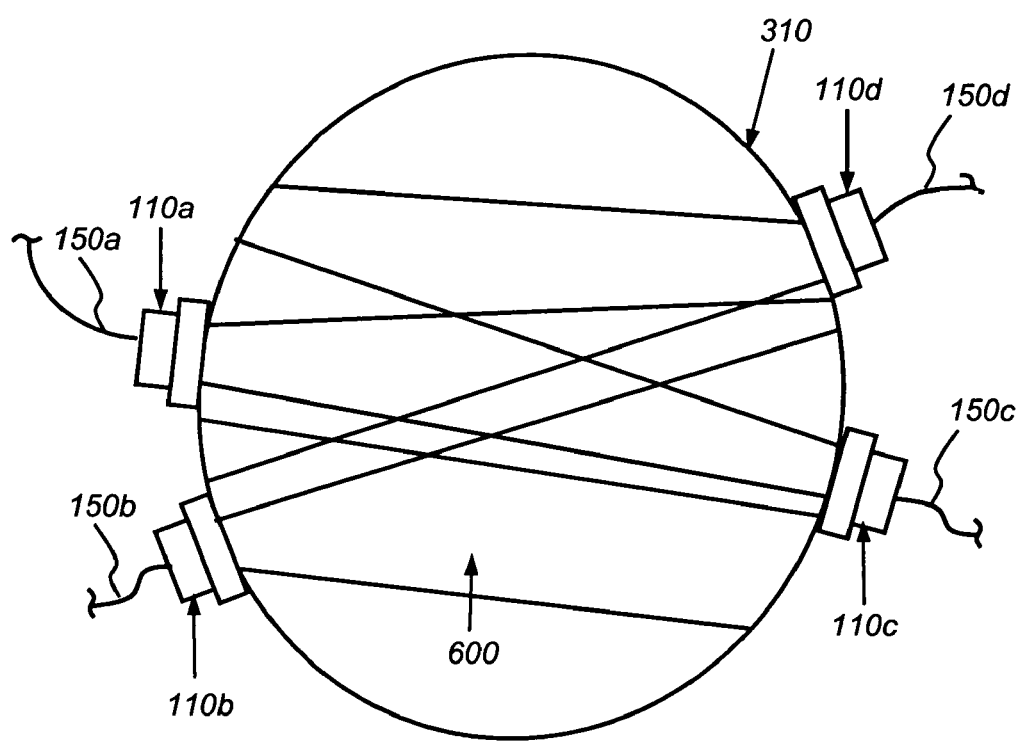
FIG. 6 is a side cross-sectional view of two pairs of LODUS transducers mounted opposite one another and a region of the brain affected by the transducers' emitted ultrasonic beams.

FIG. 6 illustrates an illustrative LODUS configuration that may be used to insonate a relatively large BBB region 600, e.g., to administer therapeutic or prophylactic agents. As shown, a first pair of LODUS transducers 110a and 110b is positioned on one side of the patient's skull, and a second pair of transducers 110c and 110d is situated approximately on the opposite side of the skull. Although each of the transducers 110a-d is illustrated as an individually-mounted transducer, at least some of the transducers may be situated in an array (not shown) of closely-packed transducer devices. Furthermore, the number of transducers applied in this illustrative embodiment may be increased or decreased without limitation. By employing many LODUS transducers 110, the average power dissipated at a given transducer can be reduced, and the total surface area over which heat is dissipated on the patient's skin increased. As such, this embodiment may be used to minimize the effects of local heating around each LODUS transducer 110a-d, especially as compared with prior focused ultrasound approaches.

The LODUS beams emitted from the first and second pairs of transducers 110a-d intersect at a relatively large region 600 of the patient's brain 310. The emitted LODUS beams may comprise separate pulse trains which are driven substantially simultaneously, e.g., by drive signals communicated over the electronic leads 150a-d, or may be time multiplexed by the control electronics, e.g., in the control module 160. Also, the transducers' operating frequencies may be modulated to reduce the effects of standing nodes and anti-nodes in the region 600.

Figure 7:
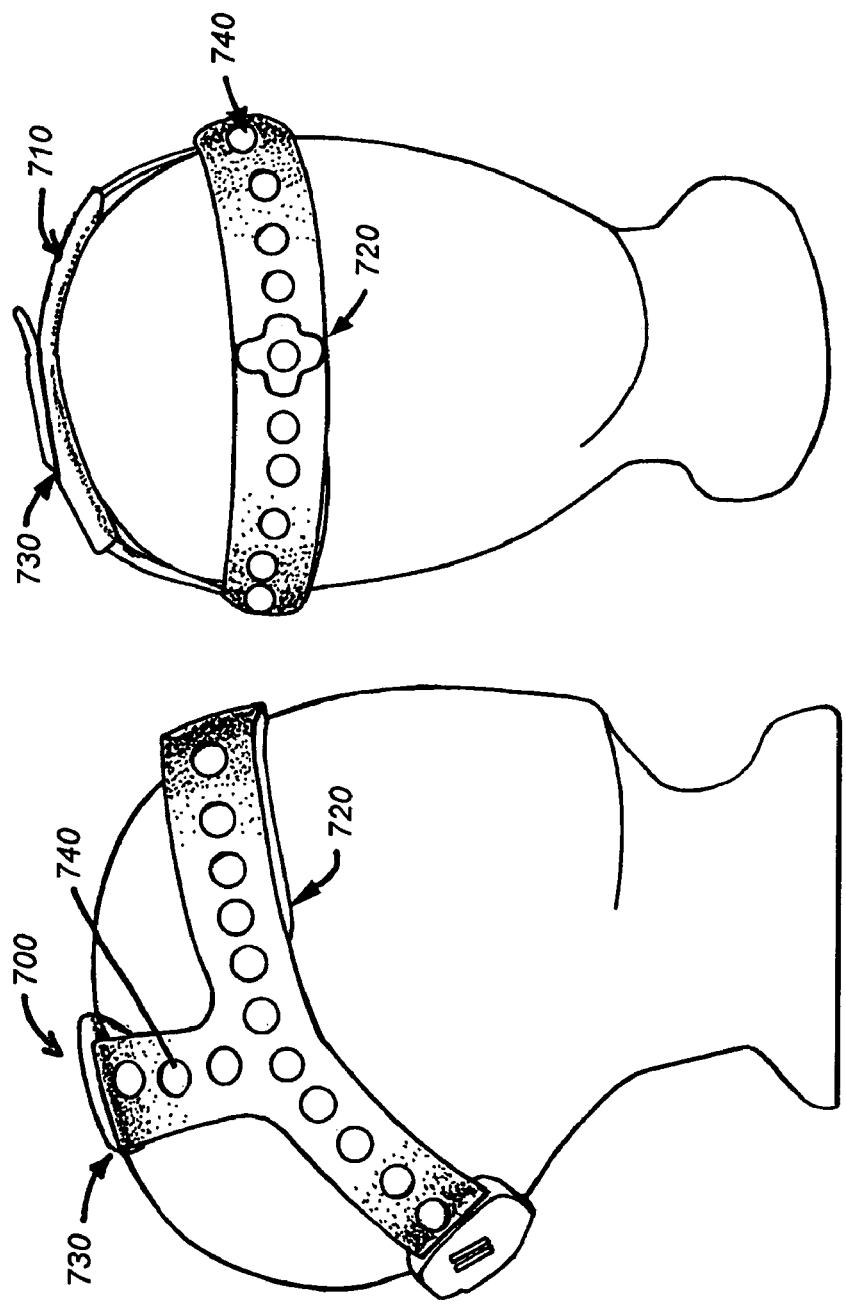
FIG. 7 are side and front views of a first exemplary headpiece that may be used to mount a plurality of LODUS transducers configured to insonate a substantial portion of a patient's brain.

FIG. 7 illustrates an exemplary headpiece 700 which supports multiple LODUS transducers (not shown) adapted to facilitate delivery of therapeutic and/or prophylactic agents through the BBB. The headpiece 700 includes a frame having a circumference band 720 and a top band 730, arranged in a similar manner as the bands 120 and 130 in the exemplary headpiece 100. The bands 720 and 730 may be adjusted to accommodate heads of various shapes and sizes. The headpiece also contains a plurality of holes 740 through which the plurality of modular LODUS transducers may be mounted.

Figure 8:
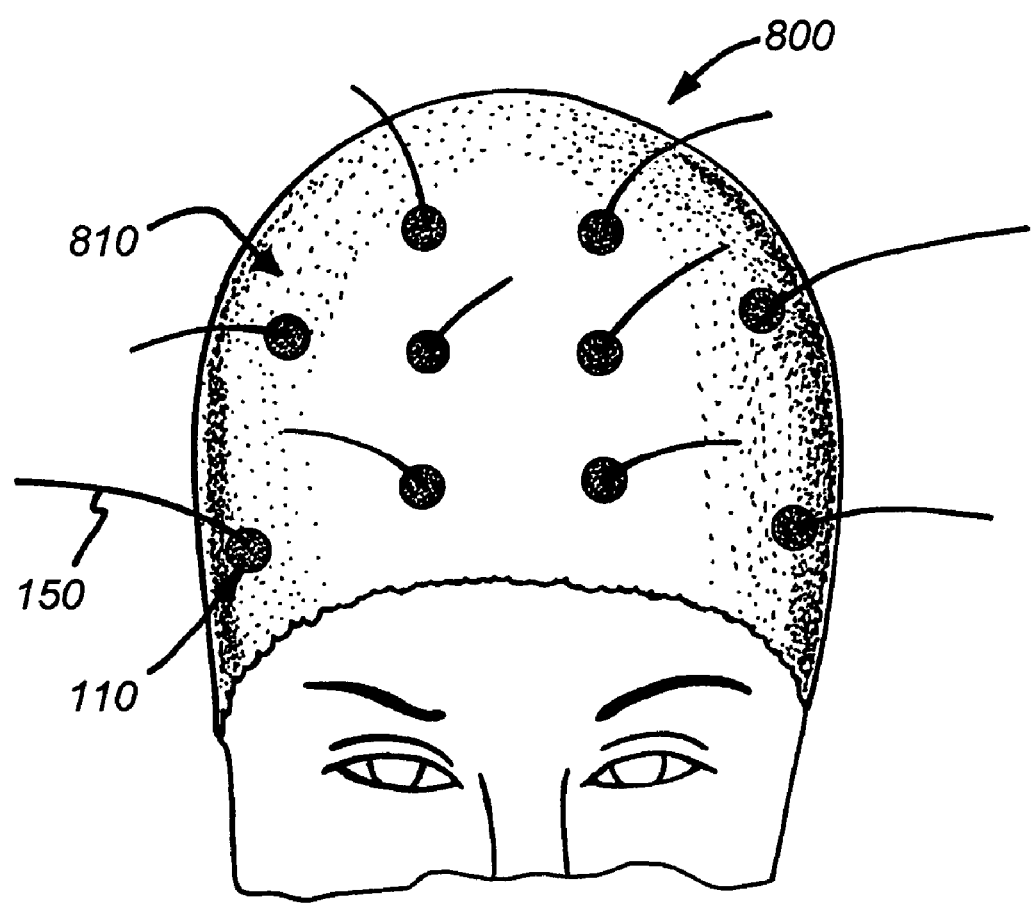
FIG. 8 is a front view of a second exemplary headpiece that may be used to mount a plurality of LODUS transducers configured to insonate a substantial portion of a patient's brain.

FIG. 8 illustrates another exemplary headpiece 800 adapted to support multiple LODUS transducers 110. In this embodiment, the headpiece is constructed of an elastic or flexible material 810, such as latex or silicone, on which the plurality of LODUS transducers 110 may be mounted. The transducers may be mounted on either an interior or exterior surface of the material 810. When mounted on the interior surface, the transducers may provide a better pressure seal against the patient's head. However, in some situations, it may be preferable to mount the LODUS transducers on the exterior surface of the headpiece 800 to facilitate connections between the electronic leads 150 and the mounted transducers. Illustratively, the transducers may be adhered to either the interior or exterior surface of the headpiece 800. Of course, those skilled in the art will appreciate that the transducers may be attached to the headpiece using other well known methods as well.

The foregoing has been a detailed description of illustrative embodiments of the invention. Various modifications and additions can be made without departing from the spirit and scope of the invention. For example, it is expressly contemplated that the control electronics and adjustable controls in the control module 160 may be implemented using functionally equivalent structures, which may be internal or external to the LODUS transducers 110. Further, the control electronics may be coupled to at least one computer-readable memory element storing instructions for implementing at least some portions of the illustrative embodiments described herein. For instance, the memory element may be programmed to select various LODUS parameters, such as operating frequency, pulse repetition frequency, mechanical index, etc.

It is also expressly contemplated that various functional equivalents may be used to implement structural aspects of the headpieces described herein. For example, the holes 730 in the headpiece 700 may be modified to interface with cooling systems or the like. Accordingly, this description is meant to be taken only by way of example and not to otherwise limit the scope of the invention.

What is claimed is:

1. A method of delivering a therapeutic or prophylactic agent through the blood-brain barrier of an animal body, comprising introducing said agent into the blood stream in the absence of exogenous bubble-forming agents and, in conjunction therewith, transiently disrupting a region of the blood-brain barrier by applying thereto low intensity directed unfocused ultrasound (LODUS) having a mechanical index of less than 1 and a frequency of less than 1.0 megahertz (MHz) to facilitate passage of said therapeutic or prophylactic agent from the bloodstream and through the blood-brain barrier.

2. The method of claim 1 in which said ultrasound is characterized by a mechanical index of approximately from 0.1 to 0.6.

3. The method of claim 1 in which said ultrasound is characterized by a frequency of approximately 300 kHz.

4. A method of delivering a therapeutic or prophylactic agent through the blood-brain barrier of an animal body, comprising introducing said agent into the blood stream in the absence of exogenous bubble-forming agents and, in conjunction therewith, transiently disrupting a region of the blood-brain barrier by sonically creating a stable oscillation of endogenous microbubbles therein by applying thereto low intensity directed unfocused ultrasound (LODUS) having a mechanical index of less than 1 and a frequency of approximately 300 kHz to thereby enable delivery of said therapeutic or prophylactic agent from the bloodstream through said region.

* * * * *